(12) United States Patent  (10) Patent No.: US 8,651,866 B2
Bulard et al.  (45) Date of Patent: Feb. 18, 2014

(54) ONE PIECE DENTAL IMPLANT AND USE THEREOF IN PROSTODONTIC AND ORTHODONTIC APPLICATIONS

(75) Inventors: Ronald A. Bulard, Ardmore, OK (US); Stephen J. Hadwin, Ardmore, OK (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/279,760

(22) Filed: Oct. 24, 2011

(65) Prior Publication Data

US 2012/0034578 A1  Feb. 9, 2012

Related U.S. Application Data

(60) Continuation of application No. 11/136,760, filed on May 25, 2005, now Pat. No. 8,043,089, which is a division of application No. PCT/US2004/010567, filed on Apr. 5, 2004, and a continuation-in-part of application No. 10/031,256, filed as application No. PCT/US00/10827 on Apr. 21, 2000, now Pat. No. 6,716,030.

(60) Provisional application No. 60/532,385, filed on Dec. 26, 2003, provisional application No. 60/464,958, filed on Apr. 23, 2003.

(51) Int. Cl.
*A61C 8/00* (2006.01)

(52) U.S. Cl.
USPC .......................................... 433/174; 606/305

(58) Field of Classification Search
USPC .................. 433/173, 174; 606/301, 305, 308
See application file for complete search history.

(56) References Cited

U.S. PATENT DOCUMENTS

| 2,836,890 A | 6/1958 | Silvas |
| 3,466,748 A | 9/1969 | Christensen |
| 3,499,222 A | 3/1970 | Linkow |
| 3,514,858 A | 6/1970 | Silverman |

(Continued)

FOREIGN PATENT DOCUMENTS

| CH | 670 563 | 6/1983 |
| DE | 3 425 737 | 2/1985 |

(Continued)

OTHER PUBLICATIONS

ASTM Designation: F 136-11, Standard Specification for Wrought Titanium-6Aluminum-4Vanadium ELI (Extra Low Interstitial) Alloy for Surgical Implant Applications (UNS R56401), 2011, pp. 1-5.

(Continued)

*Primary Examiner* — Ralph Lewis
(74) *Attorney, Agent, or Firm* — Kevin W. Weber

(57) ABSTRACT

The specification describes one-piece dental implants comprising a threaded shaft, optionally a non-circular abutment and a head having a shape which is capable of accepting a keeper cap or an O-ring, or which is capable of accepting and retaining a dental wire. The implants have dimensions that permit their use in a non-surgical method of insertion into bone, and are useful in both prosthodontic and orthodontic applications. It is emphasized that this abstract is provided to comply with the rules requiring an abstract which will allow a searcher or other reader to quickly ascertain the subject matter of the technical disclosure. It is submitted with the understanding that it will not be used to interpret or limit the scope or meaning of the claims.

15 Claims, 10 Drawing Sheets

(56) References Cited

U.S. PATENT DOCUMENTS

| | | | |
|---|---|---|---|
| 3,579,830 | A | 5/1971 | Morel |
| 3,618,212 | A | 11/1971 | Weissman |
| 3,656,236 | A | 4/1972 | Kurer |
| 3,672,058 | A | 6/1972 | Nikoghossian |
| 3,905,109 | A | 9/1975 | Cohen |
| 4,016,651 | A | 4/1977 | Kawahara |
| 4,182,034 | A | 1/1980 | McCauley |
| 4,193,194 | A | 3/1980 | Dalise |
| 4,209,905 | A | 7/1980 | Gillings |
| 4,234,309 | A | 11/1980 | Sellers |
| 4,330,891 | A | 5/1982 | Brånemark |
| 4,406,623 | A | 9/1983 | Grafelmann |
| 4,713,003 | A | 12/1987 | Symington |
| 4,746,294 | A | 5/1988 | Columbo |
| D296,362 | S | 6/1988 | Branemark |
| 4,759,714 | A | 7/1988 | Szegvary |
| 4,767,332 | A | 8/1988 | Weissman |
| 4,780,081 | A | 10/1988 | Enomoto |
| 4,793,808 | A | 12/1988 | Kirsch |
| 4,826,434 | A | 5/1989 | Krueger |
| 4,863,382 | A | 9/1989 | Bookstaber |
| 4,917,606 | A | 4/1990 | Miller |
| 5,030,094 | A | 7/1991 | Nardi |
| 5,049,072 | A | 9/1991 | Lueschen |
| 5,061,181 | A | 10/1991 | Niznick |
| 5,066,224 | A | 11/1991 | Block |
| 5,074,790 | A | 12/1991 | Bauer |
| 5,098,295 | A | 3/1992 | Dürr |
| 5,147,363 | A | 9/1992 | Härle |
| 5,194,000 | A | 3/1993 | Dury |
| 5,195,892 | A | 3/1993 | Gersberg |
| 5,211,561 | A | 5/1993 | Graub |
| 5,360,448 | A | 11/1994 | Thramann |
| 5,417,570 | A | 5/1995 | Zuest |
| 5,520,540 | A | 5/1996 | Nardi |
| 5,527,183 | A | 6/1996 | O'Brien |
| 5,538,427 | A | 7/1996 | Hoffman |
| 5,549,677 | A | 8/1996 | Dürr |
| 5,575,651 | A | 11/1996 | Weissman |
| 5,588,838 | A | 12/1996 | Hansson |
| 5,620,323 | A | 4/1997 | Bressman |
| 5,639,237 | A | 6/1997 | Fontenot |
| 5,662,475 | A | 9/1997 | Mena |
| 5,678,993 | A | 10/1997 | Jeffer |
| 5,697,779 | A | 12/1997 | Sachdeva |
| 5,702,445 | A | 12/1997 | Brånemark |
| 5,727,943 | A | 3/1998 | Beaty |
| 5,749,732 | A | 5/1998 | Sendax |
| 5,823,776 | A | 10/1998 | Duerr |
| 5,842,864 | A | 12/1998 | Unger |
| 5,885,077 | A | 3/1999 | Jeffer |
| 5,954,506 | A | 9/1999 | Tanaka |
| 5,967,772 | A | 10/1999 | Gray |
| 6,030,219 | A | 2/2000 | Zuest |
| 6,193,509 | B1 | 2/2001 | DeVincenzo |
| 6,213,775 | B1 | 4/2001 | Reipur |
| 6,270,827 | B1 | 8/2001 | Gaull |
| 6,309,215 | B1 | 10/2001 | Phan |
| 6,312,259 | B1 | 11/2001 | Kvarnström |
| 6,431,866 | B2 | 8/2002 | Hurson |
| 6,575,742 | B2 | 6/2003 | Kyung |
| 6,716,030 | B1 | 4/2004 | Bulard |
| 7,033,174 | B2 | 4/2006 | Giorno |
| 7,153,132 | B2 | 12/2006 | Tedesco |
| 7,588,988 | B2 | 9/2009 | Ahn |
| 8,043,089 | B2 * | 10/2011 | Bulard et al. ................ 433/173 |
| 2002/0127510 | A1 | 9/2002 | Kyung |
| 2002/0142265 | A1 | 10/2002 | Weissman |
| 2002/0182560 | A1 | 12/2002 | Park |
| 2003/0228556 | A1 | 12/2003 | Giorno |
| 2004/0018471 | A1 | 1/2004 | Giorno |
| 2004/0121286 | A1 | 6/2004 | Aravena |
| 2006/0029908 | A1 | 2/2006 | Allred |
| 2006/0269903 | A1 | 11/2006 | Bulard |
| 2006/0275735 | A1 | 12/2006 | Bulard |
| 2007/0090441 | A1 | 4/2007 | Ahn |
| 2008/0227056 | A1 | 9/2008 | Bulard |
| 2008/0241791 | A1 | 10/2008 | Bulard |

FOREIGN PATENT DOCUMENTS

| | | |
|---|---|---|
| DE | 3 904 237 | 8/1989 |
| EP | 0 872 216 | 10/1998 |
| EP | 1 108 398 | 6/2001 |
| EP | 1 112 723 | 7/2001 |
| FR | 1 478 557 | 4/1967 |
| MX | 05011338 | 7/2006 |
| WO | WO 00-64369 | 11/2000 |
| WO | WO 2004-093707 | 11/2004 |

OTHER PUBLICATIONS

Baumhammers, "Technique for screw-type implants", JADA Techniques, vol. 121, Sep. 1990, pp. 376-382.

Block, Implants in Dentistry, Essentials of Endosseous Implants for Maxillofacial Reconstruction, 1997, 5 pages.

Dentatus Atlas Dome Keeper Implants, advertisements, 2004, 2 pages.

Fagan, "Surgical and Prosthetic Techniques for Dental Implants", Implant Prosthodontics, For the AAIP, 1990, 6 pages.

Lesham, "Hi Tec Implants", *Dental Profit*, The Financial Dental Medicine Magazine, Dec. 1997, Tikshoret Calcalit Ltd., Israel, Issue 10, 7 pgs. (English translation).

Linkow, "Theories and Techniques of Oral Implantology", 1970, vols. I, The evolution of dental implants, pp. 140-147 and vol. II, Mandibular endosseous implant interventions, 344, 345, 358, 359, 361.

Lubit, "Vitallium Implantology", Oral Implantology, A Quarterly Review; Winter 1971, pp. 200-205.

Quinlivan, "Fabrication of a simple ball-socket attachment", Journal of Prosthodontics, Aug. 1974, vol. 32, No. 2, pp. 222-225.

Sendax, "Mini Implant Strategy Offers a Broad Range of Uses", Dentistry Today, Jan. 1995, vol. 14, No. 1, 6 pages.

International Search Report for PCT/US2004/010567 dated Oct. 21, 2004, 1 page.

Written Opinion of the International Searching Authority for PCT/US2004/010567 dated Oct. 21, 2004, 4 pages.

\* cited by examiner

FIG.5
FIG.6
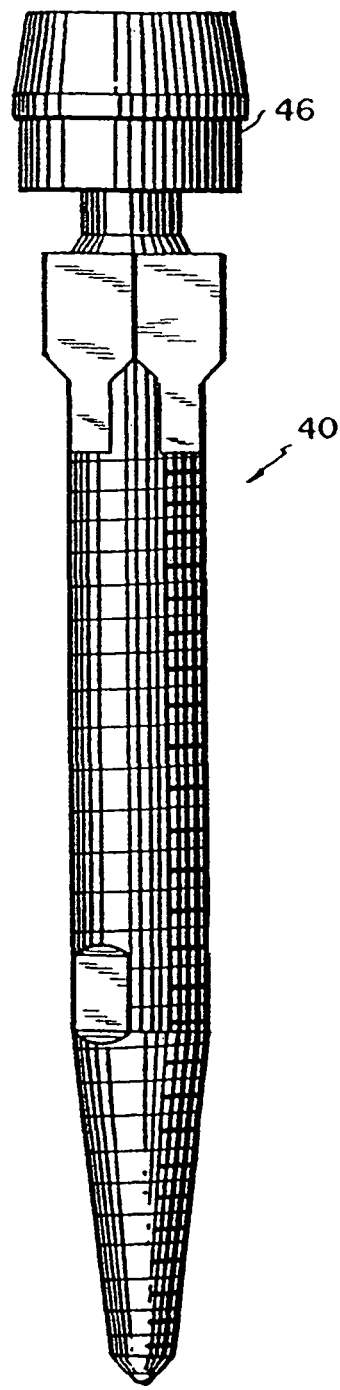
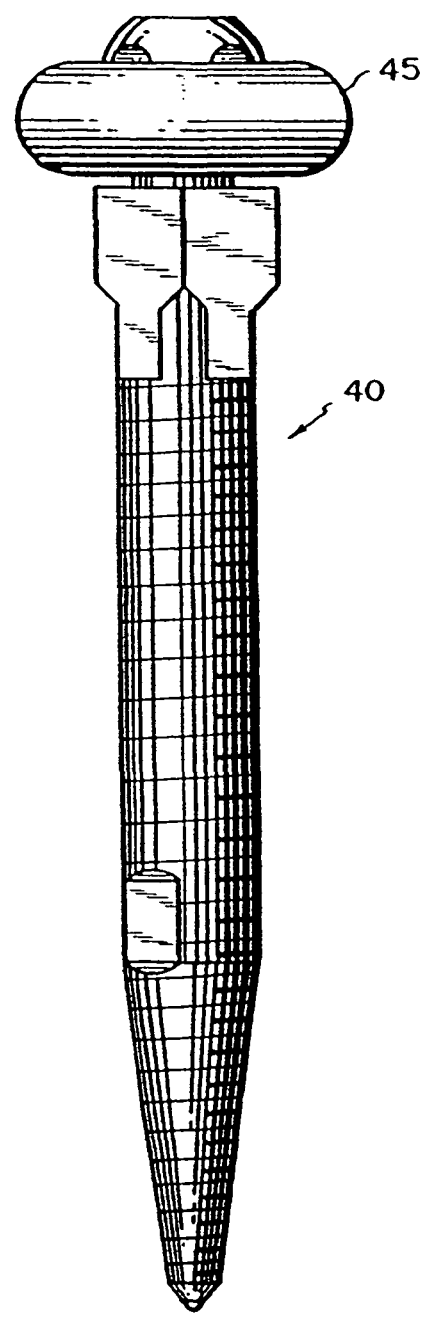

FIG.7
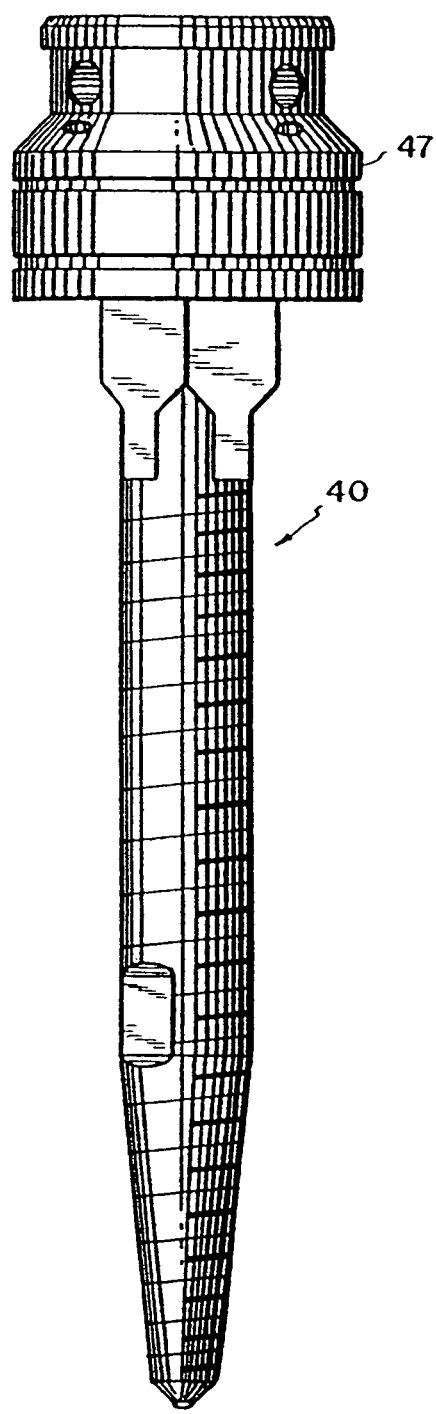
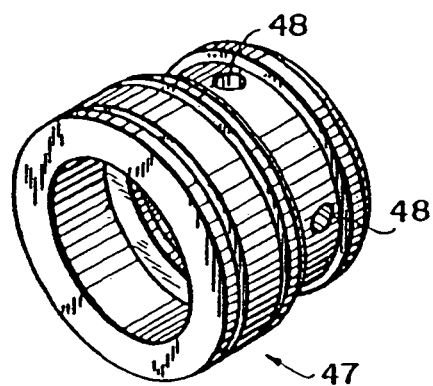
FIG.8

ONE PIECE DENTAL IMPLANT AND USE THEREOF IN PROSTODONTIC AND ORTHODONTIC APPLICATIONS

CROSS-REFERENCE TO RELATED APPLICATIONS

This application is a continuation of U.S. application Ser. No. 11/136,760, filed May 25, 2005, now pending, which is, in turn, a divisional of PCT/US2004/010567, filed Apr. 5, 2004, which is, in turn, a continuation-in-part of U.S. Ser. No. 60/532,385, filed Dec. 26, 2003, and a continuation-in-part of U.S. Ser. No. 60/464,958, filed Apr. 23, 2003; and a continuation-in-part of U.S. Ser. No. 10/031,256, filed Oct. 23, 2001, issued as U.S. Pat. No. 6,716,030 on Apr. 6, 2004, which is, in turn, a 371 of PCT/US00/10827, filed Apr. 21, 2000, which claims priority to U.S. Ser. No. 60/130,864, filed Apr. 23, 1999, the disclosures of which are incorporated by reference in their entirety herein.

BACKGROUND OF THE INVENTION

1. Field of the Invention

The present invention relates to an improved dental implant, to an improved keeper cap, and to the use of the improved implant and keeper cap for fixed or removable prosthetic applications.

2. Description of Related Art

The use of combinations of O-ring abutments and standard dental implants is well known in the art. Previously, these have not been integrated into a single device. Instead, the conventional practice has been to set one or more standard dental implant bodies, i.e., without the O-ring abutments. Thereafter, the O-ring abutments have been mounted onto the dental implant bodies, generally by screwing the O-ring abutment into the implant bodies. Then, fixed or removable prostheses have been mounted onto the combinations of the O-ring abutments and the dental implant bodies according to a variety of procedures well known in the art.

A problem with these types of fixtures is that the connections between the O-ring abutments and the dental implant bodies can loosen over time. Another problem is that these types of fixtures exhibit bacteria and ionic microleakage at the joints. It would be beneficial to have the means to avoid these problems.

A third problem is that the standard implant bodies typically are large in diameter, and this causes problems in setting these implant bodies in the bone. Specifically, surgical intervention is required, which translates to multiple office visits and increased costs, which increases both the physical and financial discomfort to the patient. This problem is addressed in the earlier U.S. Pat. No. 5,749,732, which issued on May 12, 1998 (hereinafter "the earlier patent"). The contents of the earlier patent are fully incorporated herein by reference.

The solution to this third problem as outlined in the earlier patent was to provide 1) a mini-dental implant of small diameter and strong composition, such as titanium or an alloy thereof, and 2) a non-surgical method of placing the implants comprising setting the implants directly through both gum and bone, thereby avoiding the need for surgery to incise and flap open the gum to expose the underlying bone as done previously. Because surgery was avoided, both the implants and the denture could be mounted in a single office visit, thereby reducing the cost and incidence of pain to the patient.

According to the teachings of the earlier patent, the dental implant described therein comprises a non-circular abutment, preferably of square, triangular, hexagonal or any other shape that permits threaded advance of the shaft by fingers or tools. See, the earlier patent at column 2, lines 58-60.

Therefore, it was an object of the present invention to overcome the problems associated with the conventional combinations of distinct O-ring abutments and dental implants, while at the same time provide advantages similar to those described in the earlier patent.

Further, the use of keeper caps fitted with O-ring-shaped inserts, plastic inserts, metal inserts or any other material capable of flexibly engaging with an O-ring abutment in order to removably fix a denture to an O-ring abutment is also well known. Previously, the flexibility to use either the O-ring-shaped insert or the plastic insert has not been enjoyed. Since the keeper caps are usually firmly adhered to the denture, switching from keeper caps containing O-ring-shaped inserts to those containing plastic inserts or vice versa conventionally has not been done. This is undesirable because the O-ring-shaped inserts are conventionally made of rubber, and, thus, are more gentle, and therefore have their greatest usefulness early on in the treatment when the patient's comfort level is low. However, as time passes, and the patient's comfort level rises, the use of the more rigid plastic inserts may become desirable.

Therefore, it was another object of the present invention to provide a means that would allow the practitioner to "switch" from the use of O-ring-shaped inserts to the use of plastic inserts or vice versa without having to remove the keeper cap from the denture or to form a new denture around new keeper caps.

SUMMARY OF THE INVENTION

These and other objects were met by present invention, which relates in a first embodiment to a one-piece dental implant extending between a first end and a second end, the one-piece dental implant comprising the following distinct regions integrated into one piece:
  a) a threaded shaft tapering to a point at the first end;
  b) a head at said second end; and
  c) optionally a non-circular abutment positioned between said threaded shaft and said head.

The present invention relates in a second embodiment to a keeper cap adapted to be secured to the dental implant of the invention via an O-ring-shaped insert or a plastic insert retained in said keeper cap, wherein, in the event the keeper cap is to be removably attached to a dental implant having a ball-shaped head, said keeper cap has the structure generally of first and second joined cylinders having first and second diameters, respectively, the keeper cap is closed on one end thereof, and wherein said first diameter is selected to accept and retain said O-ring-shaped insert, and said second diameter is selected to accept and retain said plastic insert.

The present invention relates in a third embodiment to a kit comprising the inventive one-piece dental implant. The kit may additionally comprise:
  a) a keeper cap adapted to be secured to said dental implant via an O-ring-shaped insert or a plastic insert retained in said keeper cap, wherein, in the event the keeper cap is to be removably attached to a dental implant having a ball-shaped head, said keeper cap has the structure generally of first and second joined cylinders having first and second diameters, respectively, the keeper cap is closed on one end thereof, and wherein said first diameter is selected to accept and retain said O-ring-shaped insert, and said second diameter is selected to accept and retain said plastic insert;

b) an O-ring-shaped insert adapted to be accepted and retained in said keeper cap and removably attached to said dental implant; and/or c) a plastic insert adapted to be accepted and retained in said keeper cap and removably attached to said dental implant.

The present invention relates in a fourth embodiment to a method of forming a removable prosthesis comprising:

a) providing the inventive kit;

b) inserting said dental implant into the jaw-bone of a patient; and c) forming said removable prosthesis around said ball-shaped or other than ball-shaped head.

In the event that a keeper cap containing said O-ring-shaped insert or said plastic insert is used, then the fourth embodiment may additionally comprise forming the removable prosthesis around said keeper cap; and securing said removable prosthesis to the jaw bone of the patient by attaching the keeper cap via said O-ring-shaped insert or said plastic insert to said dental implant.

The invention relates in a fifth embodiment to a method of forming a fixed prosthesis onto a combination of an O-ring abutment screwed into a dental implant body, comprising forming the fixed prosthesis onto the inventive one-piece dental implant.

BRIEF DESCRIPTION OF THE DRAWINGS

The invention will now be described in greater detail with reference to the drawings, wherein:

FIG. 5 is a lengthwise view of an inventive dental implant with mounted plastic insert.

FIG. 6 is a lengthwise view of an inventive dental implant with mounted O-ring-shaped insert.

FIG. 7 is a lengthwise view of an inventive dental implant with the inventive keeper cap mounted over the plastic insert (not shown) or O-ring-shaped insert (also not shown).

FIG. 8 is a perspective of an inventive keeper cap.

DETAILED DESCRIPTION OF THE INVENTION

Figure 1:
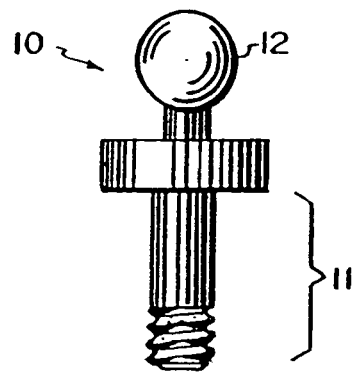
FIG. 1 is a lengthwise view of a conventional O-ring abutment to be screwed into a conventional implant body (not shown).
Figure 2:
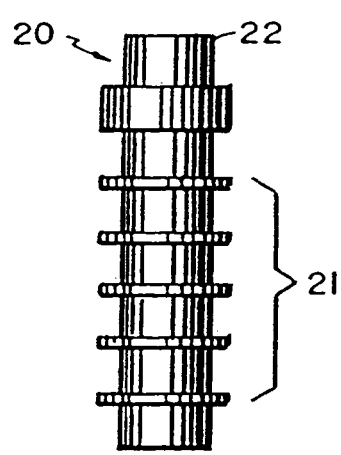
FIG. 2 is a lengthwise view of a conventional implant body, into which a conventional O-ring abutment (not shown) is screwed.
Figure 3:
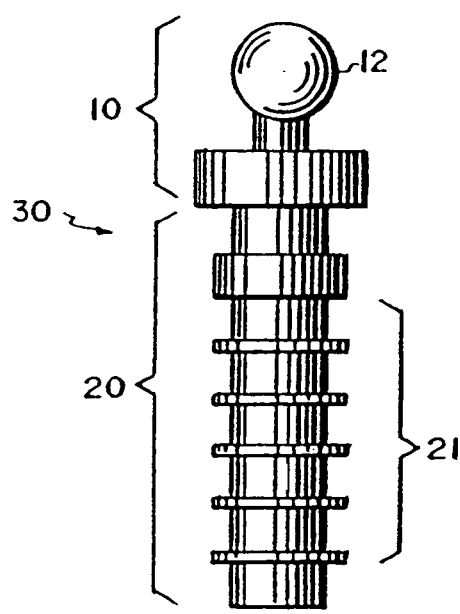
FIG. 3 is a lengthwise view of a conventional O-ring abutment screwed into a conventional implant body.

As previously discussed, the prior art made use of multiple-piece units for supporting fixed and removable prosthetic applications. Referring to FIG. 1, a first component was conventionally an O-ring abutment 10 comprising a threaded shaft 11 and ball-shaped head 12. Referring to FIG. 2, a second component was conventionally an implant body 20 comprising a threaded shaft 21 and an opening in head 22, which cooperated with and, accepted the threaded shaft of O-ring abutment 10. In practice, O-ring abutment 10 was screwed into implant body 20 to yield the construct 30 shown in FIG. 3. Since the construct shown in FIG. 3 comprised multiple parts, the bond between the component parts could loosen over time, which could be problematic.

Figure 4:
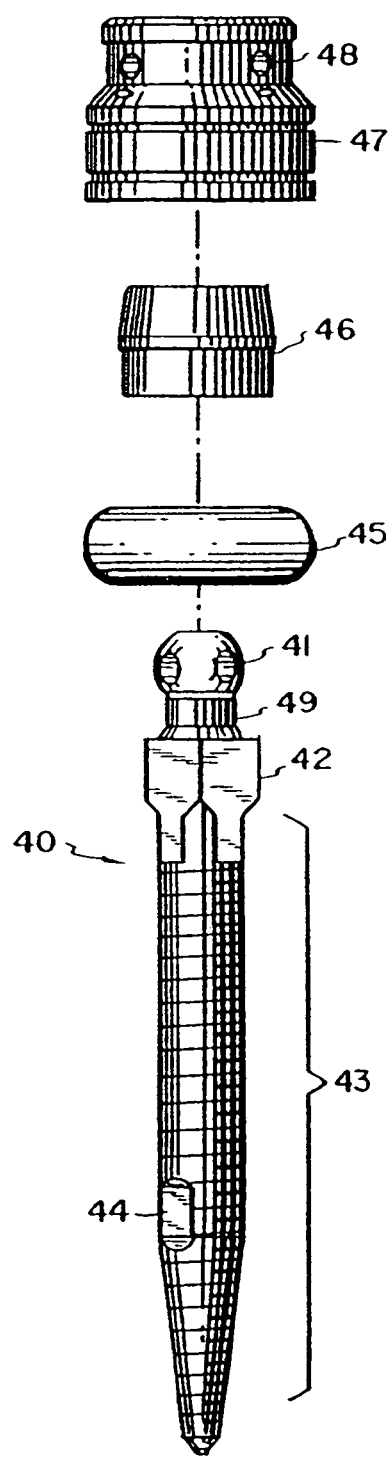
FIG. 4 is a lengthwise view of the various components of an embodiment of the present invention.
Figure 9:
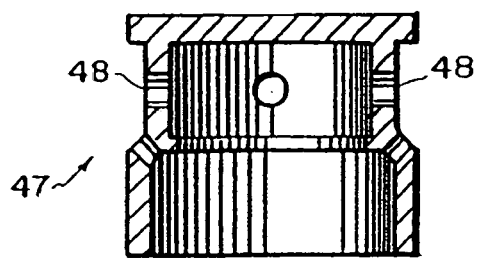
FIG. 9 is a cross-section of an inventive keeper cap.

Referring to FIG. 4, the present invention solves this problem by fully integrating the O-ring abutment and the implant body. Thus, as shown in FIG. 4, the present invention relates in a preferred embodiment to a one-piece dental implant 40 which comprises distinct but integrated ball-shaped head 41, non-circular abutment 42, and threaded shaft 43.

Figure 11:
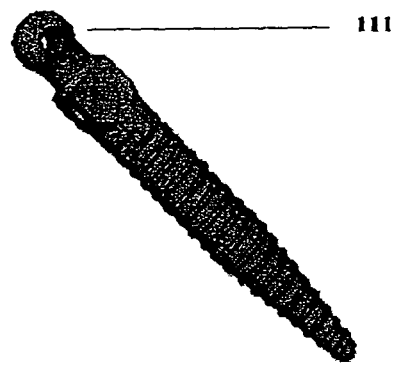
FIG. 11 is a perspective of an inventive dental implant showing holes in the implant head.
Figure 12:
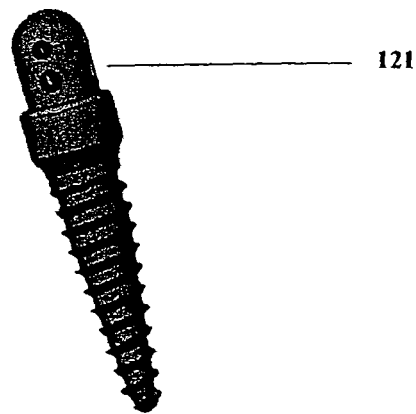
FIG. 12 is a perspective of another inventive dental implant having holes in the implant head.
Figure 13:
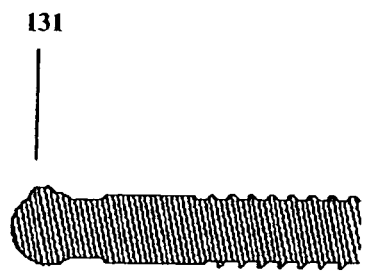
FIG. 13 is a cross-section of an inventive dental implant having an irregular head shape.
Figure 14:
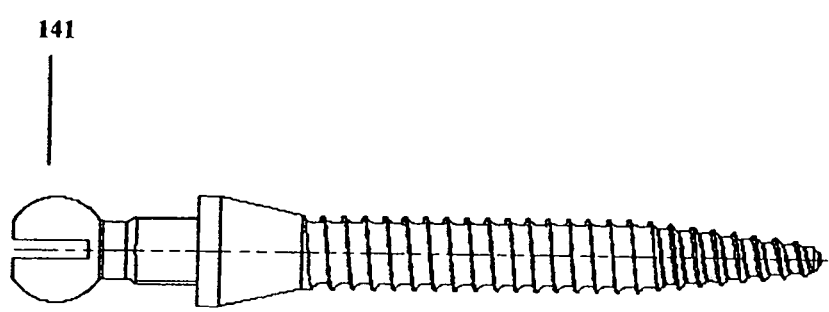
FIG. 14 is a lengthwise view of an inventive dental implant having a latched head shape capable of accepting and retaining an O-ball.
Figure 15:
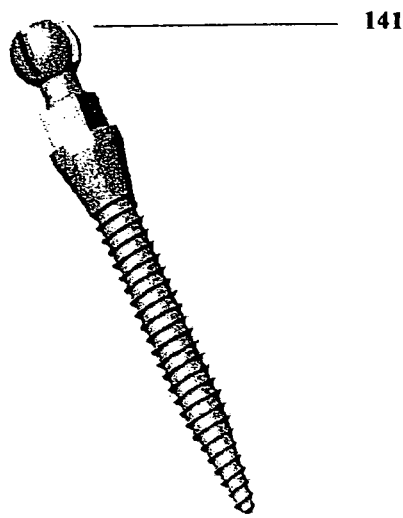
FIG. 15 is a perspective of the dental implant shown in FIG. 14.

FIG. 4 depicts a ball-shaped head 12 attached to the non-circular abutment. However, it is also possible to use a head having a shape other than ball-shaped so long as the head is capable of accepting and releasably retaining a keeper cap or an O-ring, or is capable of accepting and retaining a dental wire. Thus, in addition to being ball-shaped, the head can, for example, be in the shape of an oval, a triangle, or a mushroom, or be fitted with an i-hook, a square hole, a round hole, or a groove, or any other suitable combination of convex and concave surfaces optionally having flat portions as desired. (FIGS. 11 and 12 depict embodiments of the present invention, wherein the head of the inventive dental implant is provided with at least one hole; see elements 111 and 121 in FIGS. 11 and 12, respectively.) As illustrated in FIG. 13 by element 131, the shape can be irregular, if desired, but, as illustrated by the other figures, may also be regular. The shape of the head really is a matter of design choice, well within the skill of the ordinary practitioners in this art. Alternatively, the head can have a shape that is capable of accepting and removably retaining an O-ball, for example, an O-ball descending from the prosthesis itself. For example, as illustrated by FIGS. 14 and 15, the head of the inventive dental implant may be latched or slotted, as depicted at element 141, allowing the head to latch and grip an O-ball. In the case of an oval-shaped head, a triangle-shaped head or a mushroom-shaped head, the head can retain a conventional O-ring, but use can also be made of a keeper cap adapted to be secured to the dental implant via the O-ring or a plastic insert specifically designed to accept and releasably grip the head. The only limiting factor on the head shape is that the head be of such a shape that it is possible to secure a prosthetic device to the implant either temporarily or permanently.

Figure 16:
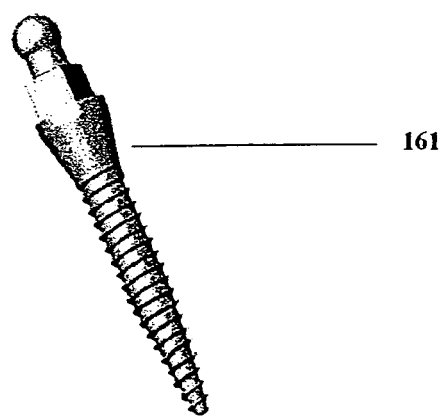
FIG. 16 is a perspective of an inventive dental implant having a tapered collar.

As depicted in FIG. 4, a portion of the shaft just beneath the non-circular abutment is unthreaded and is a mixture of curved and flattened portions. This collar can be completely round or of any other desired shape, and can be tapered, or omitted altogether. In a preferred embodiment, as illustrated by element 161 in FIG. 16, a collar is present, the collar is round, unthreaded and tapers outwardly.

According to the present invention, the dimensions of the dental implant can be varied over a wide range. The limiting factor is the suitability of the implant in the non-surgical method described in the related applications and the earlier patent. Without intending to limit the scope of the invention in any manner, as other dimensions may well prove to be suitable in the non-surgical method described herein depending upon the materials employed and the intended use, and, especially for orthodontic applications, the inventive dental implant can range in overall length from about 9 mm to about 20 mm, preferably from about 11 mm to about 13 mm. The length of the threaded shaft likewise can range from about 4 mm to about 12 mm, preferably from about 6 mm to about 8 mm; and the width of the thickest portion of the threaded shaft can range from 0.5 to about 3.0 mm, and is, preferably, about 1.8 mm.

Further, in an especially preferred embodiment, a portion of the surface of the threaded shaft contains an anti-rotational flat 44, as shown in FIG. 4, which is not threaded to reduce any (small) likelihood of unintentional rotation (unthreading) of the dental implant from the bone in which it resides. As described in the related applications and the earlier patent, this anti-rotational flat is advantageous, but not critical. When the implant comprises an anti-rotational flat, then the length of the flat in the longitudinal direction of the threaded shaft ranges in length from about 0.5 mm to about 4 mm, and is preferably about 1 mm, and the width of the threaded shaft at the flat is about 0.8 mm to about 1.8 mm, preferably about 1.2 mm. The edge of the anti-rotational flat nearest the point of the tapered shaft begins about 2 mm to about 4 mm therefrom, preferably about 3 mm therefrom. The non-circular abutment ranges in length from about 0.5 mm to about 4 mm, preferably about 1 mm in length, and has a width of about 1.4 mm to about 1.9 mm, preferably about 1.65 mm. The head, which, as indicated above, can vary in shape, ranges in length from about 0.5 mm to about 1.5 mm, and is preferably about 0.8 mm in length, and has a width of about 0.5 mm to about 1.8 mm, preferably about 1.4 mm. The head is normally attached indirectly to the non-circular abutment by a neck (illustrated as 49 in FIG. 4) of some sort, which ranges in length from about 0.5 mm to about 1.5 mm, preferably about 0.8 mm. The diameter of the circular neck, in turn, ranges from about 0.5 mm to about 1.8 mm, and is preferably about 1.4 mm. Again, these dimensions are for illustration purposes only, as were those mentioned in the related applications and the earlier patent, and the only limiting factor is the suitability of the implant in the non-surgical method described herein.

The thread design and positioning on the threaded shaft can be varied over a wide range. As shown, for example, in FIG. 10, a helix of self-tapping cutting threads 101 promotes progressive draw of the inventive dental implant into dense bone. A narrow apex of crest of thread form minimizes stress from rotational forces in penetrating dense materials, and also results in minimal torque being required to advance the inventive dental implant each revolution. Moreover, a fishbone-like shape reduces the likelihood of the inventive dental implant pulling out of bone.

In a preferred embodiment, the threaded shaft adjoins non-circular abutment 42, as shown in FIG. 4, which, because of its non-circular shape, can be grasped with a ratchet or other tool to facilitate the insertion of the dental implant into bone. The non-circular abutment ranges in length from about 1.5 mm to about 4 mm, and is preferably about 2.5 mm in length. The non-circular abutment is preferably of square, triangular, hexagonal or any other shape that permits threaded advance of the threaded shaft by fingers or tools.

The dental implant is formed of any strong metal or alloy thereof, and especially from titanium or an alloy thereof with another metal, for example, aluminum and/or vanadium. The best mode is to use a titanium alloy rod having the formula $Ti_6Al_4V$, which satisfies the American Society for Testing Materials F-136 (ASTM F-136).

Because of their small diameter compared with conventional implants, the novel implants can be placed without gum surgery. A small diameter drill is used to prepare a short cylindrical starting bore going right through the gum into the jaw bone. Because of its minute diameter there is almost no gum bleeding. As a matter of fact, the minute blood droplet on the gum serves as a marker to assist the dentist in the next step of placing the dental implant through the gum hole into the hidden-from-view jaw bone.

If desired, several drills of successively increasing diameters, but all still smaller than the dental implant diameter may be used. Other tools can be used to thread the dental implant into the jaw bone.

Figure 10A:
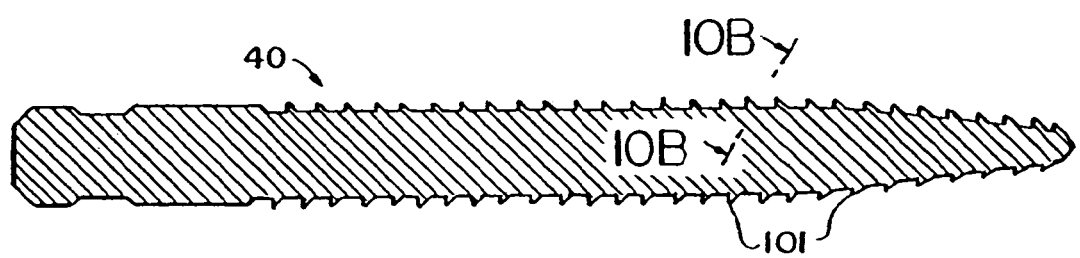
FIG. 10 is a lengthwise view of an inventive dental implant showing an exemplary thread design, which is highlighted in Detail B at a scale of 24:1, and shows a distance of 0.020 inches between threads.
Figure 10B:
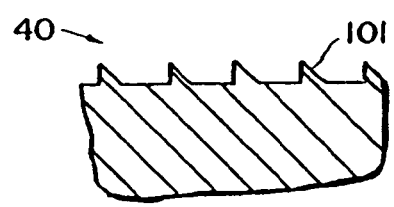

As explained above, one way of advancing the dental implant into the jaw bone is to grasp the non-circular abutment 42 with a ratchet or other tool and to use the tool to screw the dental implant into the jaw bone. As shown especially in FIGS. 4 and 10A, what is meant by "ball-shaped head" throughout this application is a head which is generally ball-shaped in appearance, but, as shown in FIGS. 4 and 10A, may have flattened portions on one or more sides thereof, and, as shown in FIG. 13, may have an irregular shape, if desired. Whether or not the head is ball-shaped and whether or not the head has flattened portions, it is possible to grasp the head instead of the non-circular abutment to advance the dental implant into the jaw bone. In the event that it is desired to advance the dental implant into the jaw bone of the patient via the dental implant head, then the non-circular abutment is superfluous and can be dispensed with altogether. Accordingly, a further embodiment of the present invention relates to the dental implant that is as described above, but lacks the non-circular abutment. In other words, in its simplest form the inventive dental implant need only comprise the threaded shaft and the ball-shaped or other than ball-shaped head integrated into a one-piece design.

Alternatively, the head may be adapted to accept a tool, for example, by providing the head with a hole into which a tool, for example, a rod or some other tool capable of being grasped and turned, may be inserted. See, again, FIGS. 11 and 12. Once the head is fitted with the tool, it will be possible to grasp the tool and to turn the tool to advance the dental implant into the bone.

If desired, the dentist can even shape the placed abutment heads if he/she deems it advisable for parallelism.

Figure 17:
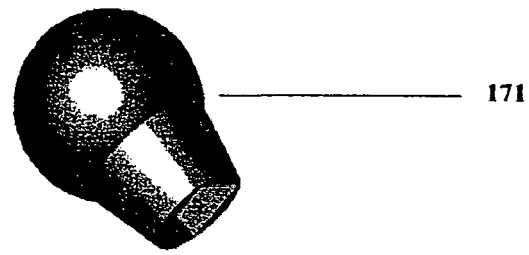
FIG. 17 is a perspective of an inventive retrofit ball.
Figure 18:
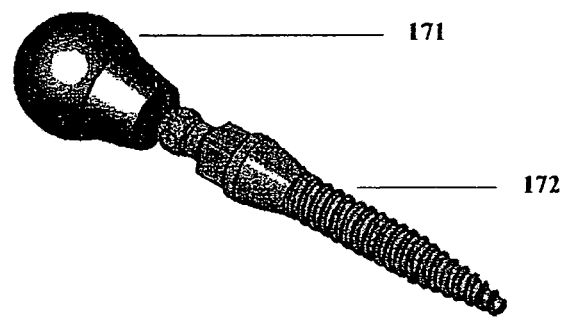
FIG. 18 is a perspective of an inventive retrofit ball being assembled onto an inventive dental implant having an O-ball head.
Figure 19:
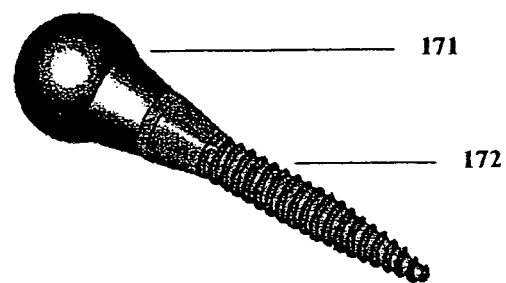
FIG. 19 is a perspective of the assembled elements depicted in FIG. 18.

In the event that the implant heads become overused in some manner or it is desirable to change the shape of the head in some manner, it may be desirable to retrofit the dental implant with a new head. FIG. 17 illustrates a retrofit head 171, which, for the purposes of this illustration only, is ball-shaped. This retrofit head can be fitted over the existing dental implant head as depicted in FIGS. 18 and 19 to provide the dental implant with a new head. As depicted in FIGS. 17-19, the retrofit head is ball-shaped and is being placed on top of a dental implant with a ball-shaped head. However, as indicated above, this is for illustration purposes only, and it is possible that either one or both of the retrofit head and the dental implant head will be other than ball-shaped.

The ultra-small width of the inventive dental implant makes it uniquely possible for the inventive dental implants to be inserted directly through the soft tissue into the underlying bone without any flap surgery incisions or sutures making for a much more patient-friendly procedure than is typical of conventional implant systems.

Further, the ultra-slim width permits a minimal encroachment on usually sparse amounts of good quality tough epithelialized gum tissue making it all the more likely that the dental implant will be more comfortable not only at time of placement but during the aftercare period and beyond.

Thus, the inventive dental implants can be placed using the same non-surgical method as described in the related applications and the prior patent, and all pertinent details are fully incorporated herein by reference.

Because the inventive dental implants have a one-piece design, they are not susceptible to the microleakage problems on the bacteria and ionic levels, which were characteristic of the prior art multiple-piece designs. Accordingly, the inventive dental implants are less likely to be rejected by the patient, less likely to lead to infection, and less likely to corrode.

Once the inventive dental implants have been positioned, they can be used for prosthodontic application, for example, both fixed and removable prosthetic applications, and also for orthodontic applications. The details of these procedures are well known to persons having ordinary skill in the art, and, therefore, these well known details are not repeated here. See, for example, Michael S. Block et al., *Implants in Dentistry*, W. B. Saunders Company, Philadelphia, Pa., 1997, the entire contents of which are incorporated herein by reference.

For prosthodontic applications, the implants are advantageously positioned along the apex-line for the jaw bone. While desirably parallel, they might not be absolutely so but this does not pose a problem in the multiple placements and removals of the denture during fitting. Boring out the anchor holes in the denture bottom accommodates each fitting the final hardening locking the abutment heads in place.

For orthodontic applications, the implants are positioned where necessary to provide proper anchoring or other support, as is well known in the art. Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and O-rings. The brackets and bands are bonded to the patient's teeth using a suitable material, such as dental adhesive. Once the adhesive has set, the archwire is attached to the brackets by way of slots in the brackets. The archwire links the brackets together and exerts forces on them to move the teeth over time. Twisted wires or elastomeric O-rings are commonly used to reinforce attachment of the archwire to the brackets. Attachment of the archwire to the brackets is known in the art of orthodontia as "ligation" and wires used in this procedure are called "ligatures." The elastomeric O-rings are called "plastics."

After the archwire is in place, periodic meetings with the orthodontist are required, during which the patient's braces will be adjusted. This involves installing different archwires having different force-inducing properties or by replacing or tightening existing ligatures. Between meetings, the patient may be required to wear supplementary appliances, such as elastic bands or headgear, to supply additional or extraoral forces.

Although conventional braces are effective, they are often a tedious and time consuming process requiring many visits to the orthodontist's office. Moreover, from a patient's perspective, they are unsightly and uncomfortable.

Anchoring of archwires to the inventive implants will dispense with the need for some supplementary appliances, for example, the wearing of headgear. This will improve the patient's self-esteem and comfort.

Referring to FIGS. 5-9, in an especially preferred embodiment, use is made of the inventive keeper cap 47 to mount a removable prosthesis, for example, a denture (not shown), to the ball-shaped head region (not shown) of dental implant 40. The keeper cap, as discussed above, is adapted to accept and retain either O-ring-shaped insert 45 or plastic insert 46, which, in turn, removably attaches, in this illustrative embodiment, to the ball-shaped head of dental implant 40. The keeper cap 47 can be made of any conventional material, and is preferably made from the same material as the dental implant, i.e., titanium or from an alloy of titanium with another metal, for example, aluminum and/or vanadium. The best mode is to use a titanium alloy rod having the formula $Ti_6Al_4V$, which satisfies ASTM F-136. Once the prosthetic attachment cap is mounted, the prosthesis can be formed in the conventional manner.

In a preferred embodiment, the keeper cap has an interior diameter in the portion that accepts and retains the O-shaped ring insert of from about 2 mm to about 6 mm, and is preferably about 4.5 mm in interior diameter. The interior diameter of the portion that accepts and retains the plastic insert ranges from about 2 mm to about 4 mm, and is preferably about 3.1 mm in interior diameter.

In an especially preferred embodiment, the portion of the keeper cap that accepts and retains the plastic insert is fitted with one or more dimples 48, as shown, for example, in FIG. 8. These dimples serve two primary functions. First, they prevent the rotation of the keeper cap in the prosthesis once the acrylic plastic is set. Second, their presence compresses the wall of the keeper cap at that location, and this allows the plastic insert to snap into place.

An advantage of the inventive keeper cap is that its use permits the switching from O-ring inserts or plastic inserts. To remove a plastic insert from the keeper cap, a reaming instrument is used to thin out or ream out the inner wall of the plastic insert sufficiently so it is thin enough to deform by cutting or pressing it centrally until it crumples and can be readily excavated out of the keeper cap. To install a plastic insert, the plastic insert is pressed into the keeper cap until it snaps into place, partially aided internally by the presence of the little dimples on the inner wall of the keeper cap.

Instead of using the inventive keeper cap, it is also possible to use conventional keeper caps having either O-ring-shaped inserts or plastic inserts or other inserts, for example, metal or nylon inserts. Again, once the prosthetic attachment cap is mounted, the prosthesis can be formed in the conventional manner.

Alternatively, it is possible to place a shim, or tubular spacer, around the dental implant prior to mounting the prosthesis so as to facilitate the removal of the prosthesis later. This can be particularly useful where the prosthesis is built up over several office visits.

The following non-limiting exemplary protocol illustrates practice of the present invention with an illustrative inventive dental implant containing a ball-shaped head and a non-circular abutment for the purposes of illustration only:

Example

1. Jaw Anatomy Evaluation

The clinician should palpate the labio-lingual or bucco-lingual width dimensions to estimate the optimal direction and angulation for exploratory drill entry through crestal soft tissue then through the cortical bone layer and finally, four to five millimeters into the underlying medullary bone. Bone calipers may also be used to estimate actual bony width, once crestal soft tissue anesthesia is obtained. A point probe may also be used to advantage in estimating soft tissue depth and quality of the underlying bone.

2. Drill Specifications

An appropriate drill may be a tapered 700 XI or 700 XXI 1010 or 1012 carbide fissure bur or tapered diamond drill (coarse grain is preferable) used in a friction grip-water-cooled air turbine handpiece. This precision tool is carefully speed controlled by a foot rheostat to provide adequate torque while achieving minimal heat production.

3. Drill Technique

The required drilling is really a micro-addition in comparison to larger scale drilling operations for conventional implants. The primary idea here is to ignore the concept of a precise osteotomy and think of the site procedure as comparable to developing a minimal "starter" hole.

4. Placement of Dental Implants

The placement of a dental implant into the pilot opening through overlying attached gingiva on the ridge crest is facilitated using a small implant carrier device and then using the same device to initiate the self-tapping process by turning the carrier clockwise between thumb and index finger while exerting downward pressure on the abutment held in the long axis of the implant. This process provides the initial "take" into bone of the threaded portion of the implant body, and is enhanced by the presence of the small "flat" without threads, which is advantageously located about one-third the distance from the apex of the implant, which permits any small bony particle accumulation to build up in the area of the "flat" helping to avoid a significant interference with the ongoing insertion process, and with time in situ, acting also as an autogenous bone graft focus, or stop which when fully calcified functions as an implant anti-rotation barrier, reducing the likelihood that any istrogenic counterclockwise moments of force could work negatively to back out the implant. This anti-rotation feature is probably not critical to routine success of a dental implant but is added insurance especially for long-term applications.

A winged thumb screw or analogous tool is used to continue the implant insertion process as soon as noticeable bony resistance is experienced and a more efficient tool is indicated. The wings of this device permit more thumb and finger purchase and control than the carrier tool. The thumb screw is kept in play until once again obvious resistance is encountered during the insertion process.

Ratchet and abutment head adapter tools are next utilized for the final stage of implant insertion, where carefully controlled, small incremental ratchet turns will provide efficient self-tapping in everything except the very densest of bone and assurance that the implant will demonstrate a rocklike integration with the bone that can then indeed be immediately loaded for functionability. For extremely dense bone sites experienced at deep levels it may be preferable not to try and force the insertion process, but rather to reverse the ratchet and back out the implant. It is then entirely possible to drill through the dense bone. The implant may then be reintroduced into the self-tapped site with carrier and thumb screw devices until once again resistance is met, at which point the ratchet and adapter are again employed to finalized the seating of the implant up to its abutment head protruding from the gingival soft tissue at its full length but with no neck or thread portions visible ideally.

5. Reconstruction

The reconstructive protocol is based on three elements: (a) The universal O-ball abutment functions as an all-purpose abutment for both removable and fixed applications (and for both transitional and long-term applications), permitting for the first time in implant prosthodontics a single one piece implant to provide this range of options. (b) The Elastomeric Shim (or spacer) eliminates angulation problems from both transitional and long term applications (and simplifies the complete lab process.) (c) The "Ponabut" design for fixed prosthetic applications (both transitional and long-term) provides maximum aesthetic, phonetic and hygienic design options.

Additionally, for transitional applications, a reinforcement system, utilizing either intertwined (paired) stainless steel ligature twists, or IMTEC Titanium Mesh strips, or a combination of the two, is recommended to provide additional strength for such transitional prosthodontics cases, with particular benefits demonstrable for close bite problem situations.

If a removable application is called for by the treatment plan the O-ball design can provide support for a transitional removable full or partial denture including the overdenture type. The attachments can be either the O-ring type for slightly less forceful gripping of the abutment head or the plastic type cap which has a somewhat more positive retentive grip while still providing some rotational compliance. The most forgiving attachment is the O-ring type and is probably the attachment of choice if there is any doubt at the outset as to the degree of bony integration upon insertion of the dental implant. Graduating from O-Ring to plastic attachment is entirely possible as a routine progression where indicated by the need for more positive retentive force, since the total replacement of one attachment for another is a matter of a brief intraoral procedure which is readily accomplished.

Step-by-step, the intra-oral retrofit of any removable prosthesis utilizing the O-ball abutment and keeper cap with either an O-ring attachment or plastic attachment, is as follows. Transfer the head position of the abutment(s) to the removable prosthesis tissue bearing undersurface. Using an acrylic laboratory carbide or equivalent instrument, excavate out the area of the abutments. Lubricate the abutment head(s) with a thin Vaseline coating, place an elastomeric shim (spacer) over the cervical half of the abutment while permitting the O-ball half of the abutment to protrude uncovered. As an additional protective option, place a small circle of latex rubber (punched out in the center with the smallest rubber dam hole) over the O-ball head until it rests on the lower half of the abutment shoulder which is prevented from further cervical progression by the presence of the elastomeric shim (or spacer). The keeper cap with rubber O-ring inserted, or with plastic insert, are then placed over the O-ball until fully seated and tested for easy rotational compliance. Refit the removable denture with the relieved openings over the attachments to test again for adequate passivity and clearance, and insert over the attachments intraorally, instructing the patient to close gently but firmly into centric occlusion, and allowing acrylic resin to cure fully and hard set.

The above technique is essentially the same for producing either transitional or long-term fixed prosthodontics. Preferably, an elastomeric shim is slipped over the abutment prior to waxing up for a casting or overlaying to produce an acrylic restoration.

It should be understood that the preceding is merely a detailed description of one preferred embodiment or a small number of preferred embodiments of the present invention and that numerous changes to the disclosed embodiment(s)

can be made in accordance with the disclosure herein without departing from the spirit or scope of the invention. The preceding description, therefore, is not meant to limit the scope of the invention in any respect. Rather, the scope of the invention is to be determined only by the appended issued claims and their equivalents.

What is claimed is:

1. A dental implant comprising:
   a one-piece dental implant that extends between a first end and a second end along a longitudinal axis, and wherein the one-piece dental implant comprises the following distinct regions integrated into one piece:
   an elongated shaft including a cylindrical portion and a tapered portion, the cylindrical portion and the tapering portion each including threads;
   a head at the second end of the dental implant, wherein the head is not threaded;
   an unthreaded abutment positioned between the threads of the shaft and the head, wherein the abutment has a non-circular configuration when viewed in directions coincident with the longitudinal axis and comprises a flat surface extending in parallel with the longitudinal axis; and
   a neck coupling the head to the abutment, the neck including a smaller diameter than the head; and
   a collar positioned between the threaded shaft and the abutment, the collar being unthreaded and including both flat and curved surfaces oriented parallel to the longitudinal axis.

2. The dental implant according to claim 1, wherein the threaded shaft comprises self-tapping cutting threads enabling the dental implant to be self-tapped through and beyond a starting bore 4 to 8 mm in length through a patient's gum and into the patient's jawbone below, said starting bore being smaller in diameter than said implant.

3. The dental implant according to claim 2, wherein self-tapping cutting threads further enable the dental implant to be seated in said jawbone with sufficient integration to permit immediate loading of the implant for functionability.

4. The dental implant according to claim 2, wherein the self-tapping cutting threads have a fishbone shape.

5. The dental implant of claim 1, wherein the head includes a shape which is capable of accepting and releasably retaining a keeper cap or an O-ring, or which is capable of accepting and retaining a dental wire, or which is capable of accepting and releasably retaining an O-ball.

6. The dental implant of claim 5, wherein the shape of the head comprises convex and/or concave elements and is other than ball-shaped.

7. The dental implant of claim 1, wherein the head is capable of accepting and releasably retaining a keeper cap.

8. The dental implant of claim 1, wherein the head is capable of accepting and releasably retaining an O-ring.

9. The dental implant of claim 1, wherein the head is capable of accepting and releasably retaining an O-ball.

10. The dental implant of claim 1, wherein the dental implant has an overall length from 9 mm to 20 mm.

11. The dental implant of claim 10, wherein the dental implant has an overall length between 11 mm and 13 mm.

12. The dental implant of claim 1, wherein the elongated shaft has a length between 4 mm and 12 mm.

13. The dental implant of claim 12, wherein the elongated shaft has a length between 6 mm and 8 mm.

14. The dental implant of claim 1, wherein the non-circular abutment has a length between 1.5 mm and 4 mm.

15. A combination comprising:
    a) a dental implant according to claim 1; and
    b) a retrofit head adapted to fit over the head of said dental implant and to be secured to said dental implant, said retrofit head itself having a head having a shape which is capable of accepting and releasably retaining a keeper cap or an O-ring, or which is capable of accepting and retaining a dental wire, or which is capable of accepting and releasably retaining an O-ball.

* * * * *

UNITED STATES PATENT AND TRADEMARK OFFICE
CERTIFICATE OF CORRECTION

PATENT NO. : 8,651,866 B2  
APPLICATION NO. : 13/279760  
DATED : February 18, 2014  
INVENTOR(S) : Ron Bulard et al.

Page 1 of 1

It is certified that error appears in the above-identified patent and that said Letters Patent is hereby corrected as shown below:

On the Title Page, Item (54) and in the Specification, Column 1, Line 2, (Title)
Delete "PROSTODONTIC" and insert -- PROSTHODONTIC --, therefor.

Page 2, Item (56) Column 2 (Other Publications)
Line 13, delete "Vols." and insert -- Vol's. --, therefor.

Signed and Sealed this
Seventeenth Day of February, 2015

Michelle K. Lee
*Deputy Director of the United States Patent and Trademark Office*